(12) United States Patent
Friedenberg

(10) Patent No.: US 12,151,101 B2
(45) Date of Patent: Nov. 26, 2024

(54) NON-INVASIVE EYE-TRACKING CONTROL OF NEUROMUSCULAR STIMULATION SYSTEM

(71) Applicant: Battelle Memorial Institute, Columbus, OH (US)

(72) Inventor: David A. Friedenberg, Columbus, OH (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 709 days.

(21) Appl. No.: 16/200,145

(22) Filed: Nov. 26, 2018

(65) Prior Publication Data

US 2019/0091472 A1    Mar. 28, 2019

Related U.S. Application Data

(63) Continuation-in-part of application No. 15/578,756, filed as application No. PCT/US2016/035503 on Jun.
(Continued)

(51) Int. Cl.
*A61N 1/36* (2006.01)
*A61B 3/00* (2006.01)
(Continued)

(52) U.S. Cl.
CPC ........ *A61N 1/36031* (2017.08); *A61B 3/0091* (2013.01); *A61B 3/145* (2013.01);
(Continued)

(58) Field of Classification Search
CPC ........... A61F 2/68; A61H 1/02; A61H 1/0237; A61H 1/0274; A61H 1/0285; A61H 3/00;
(Continued)

(56) References Cited

U.S. PATENT DOCUMENTS

| | | | | |
|---|---|---|---|---|
| 4,836,670 A | * | 6/1989 | Hutchinson | ............ A61B 3/113 351/210 |
| 6,847,336 B1 | * | 1/2005 | Lemelson | ............... G16H 20/40 345/8 |

(Continued)

FOREIGN PATENT DOCUMENTS

| WO | WO 2006/074029 A2 | 7/2006 |
|---|---|---|
| WO | WO 2014/089266 A2 | 6/2014 |
| WO | WO 2016/196784 A1 | 12/2016 |

OTHER PUBLICATIONS

Merriam-Webster scale definition.*

*Primary Examiner* — Alyssa M Alter
*Assistant Examiner* — Jessandra F Hough
(74) *Attorney, Agent, or Firm* — Lippes Mathias LLP

(57) ABSTRACT

A non-invasive control system for neuromuscular stimulation includes an eye-tracking device, an electrical stimulation device, and software that interprets the eye movements of the user to determine an intended movement and sends electrical signal(s) to the stimulation device to achieve the intended movement. For example, the stimulation device may be a sleeve with electrodes worn on a paralyzed limb, with the intended movement being the movement of the limb.

14 Claims, 8 Drawing Sheets

Related U.S. Application Data 2, 2016, now abandoned, application No. 16/200,145 is a continuation-in-part of application No. PCT/US2017/034192, filed on May 24, 2017.

(60) Provisional application No. 62/342,140, filed on May 26, 2016, provisional application No. 62/169,810, filed on Jun. 2, 2015.

(51) Int. Cl.

| | |
|---|---|
| *A61B 3/113* | (2006.01) |
| *A61B 3/14* | (2006.01) |
| *A61B 5/00* | (2006.01) |
| *A61B 5/16* | (2006.01) |
| *A61F 2/68* | (2006.01) |
| *A61F 4/00* | (2006.01) |
| *A61G 5/04* | (2013.01) |
| *A61H 1/02* | (2006.01) |
| *A61H 3/00* | (2006.01) |
| *A61N 1/04* | (2006.01) |
| *B25J 9/00* | (2006.01) |
| *B25J 9/16* | (2006.01) |

(52) U.S. Cl.
CPC ............ *A61B 5/163* (2017.08); *A61B 5/4836* (2013.01); *A61F 2/68* (2013.01); *A61F 4/00* (2013.01); *A61G 5/04* (2013.01); *A61H 1/02* (2013.01); *A61H 1/0237* (2013.01); *A61H 1/0274* (2013.01); *A61H 1/0285* (2013.01); *A61H 3/00* (2013.01); *A61N 1/36003* (2013.01); *B25J 9/1694* (2013.01); *A61B 3/113* (2013.01); *A61H 2201/1207* (2013.01); *A61H 2201/1635* (2013.01); *A61H 2201/164* (2013.01); *A61H 2201/165* (2013.01); *A61H 2201/501* (2013.01); *A61H 2201/5064* (2013.01); *A61H 2201/5079* (2013.01); *A61H 2201/5084* (2013.01); *A61H 2201/5097* (2013.01); *A61N 1/0452* (2013.01); *A61N 1/0476* (2013.01); *A61N 1/0484* (2013.01); *B25J 9/0006* (2013.01); *G05B 2219/35503* (2013.01)

(58) Field of Classification Search
CPC .... A61H 2201/1207; A61H 2201/1635; A61H 2201/164; A61H 2201/165; A61H 2201/501; A61H 2201/5064; A61H 2201/5079; A61H 2201/5084; A61H 2201/5097; B25J 9/1694; B25J 9/0006; G05B 2219/35503; A61N 1/36031; A61N 1/36003; A61N 1/0452; A61N 1/0476; A61N 1/0484; A61B 5/163; A61B 5/4836; A61B 3/0091; A61B 3/145; A61B 3/113; A61G 5/04
See application file for complete search history.

(56) References Cited

U.S. PATENT DOCUMENTS

| | | | |
|---|---|---|---|
| 2003/0120183 A1* | 6/2003 | Simmons | G06F 3/011 |
| | | | 600/595 |
| 2009/0312817 A1 | 12/2009 | Hogle et al. | |
| 2010/0286748 A1 | 11/2010 | Midani et al. | |
| 2011/0307079 A1 | 12/2011 | Oweiss et al. | |
| 2013/0085317 A1* | 4/2013 | Feinstein | A61F 5/01 |
| | | | 600/14 |
| 2014/0200432 A1 | 7/2014 | Banerji et al. | |
| 2016/0022137 A1* | 1/2016 | Wetzel | A61B 3/113 |
| | | | 600/558 |
| 2016/0235323 A1* | 8/2016 | Tadi | A61B 5/7285 |
| 2017/0340504 A1* | 11/2017 | Sanz Merodio | A61H 3/00 |

* cited by examiner

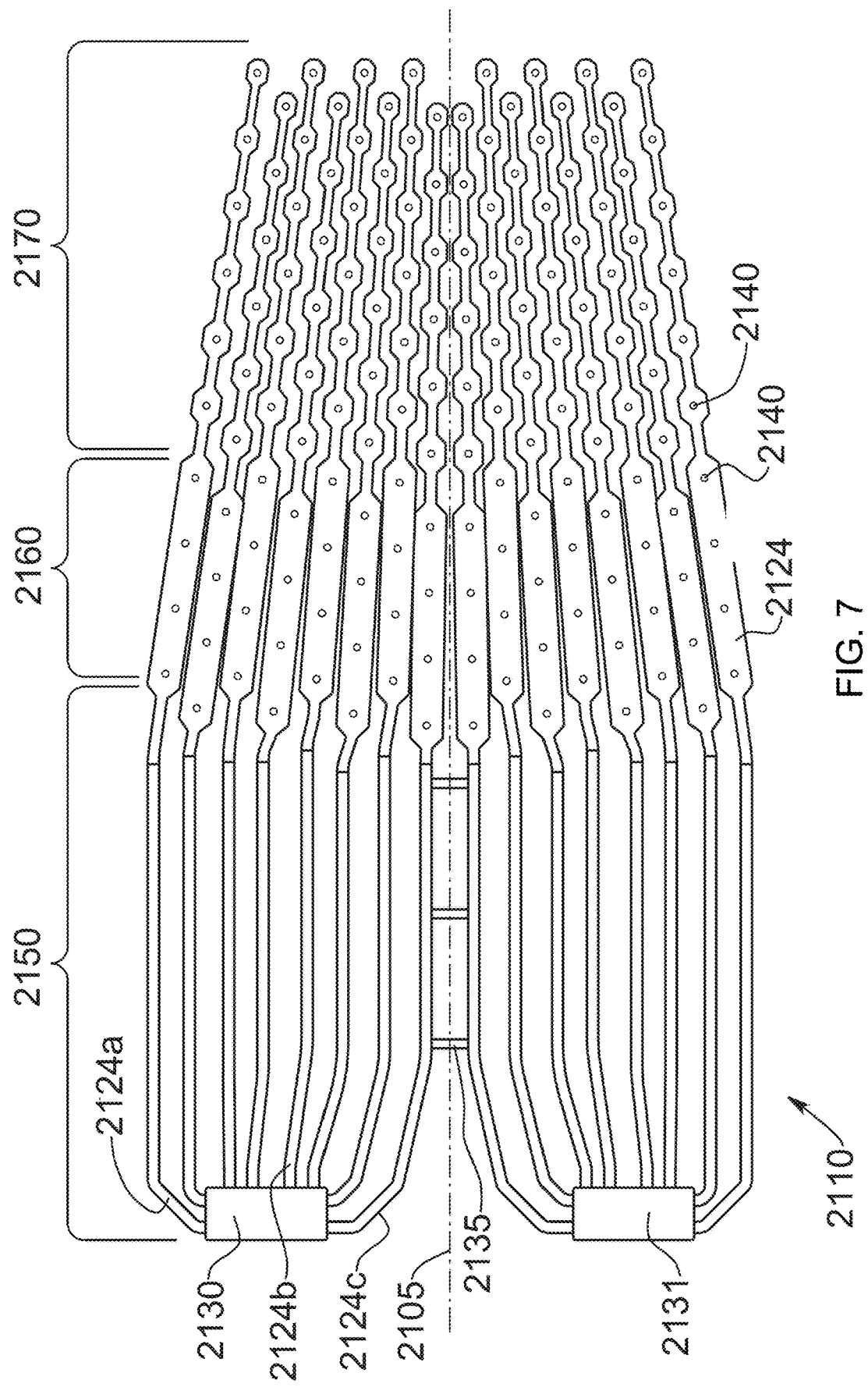

NON-INVASIVE EYE-TRACKING CONTROL OF NEUROMUSCULAR STIMULATION SYSTEM

CROSS-REFERENCE TO RELATED APPLICATIONS

This application is a continuation-in-part of PCT Application No. PCT/US2017/034192, filed on May 24, 2017, which claimed priority to U.S. Provisional Patent Application Ser. No. 62/342,140, filed on May 26, 2016. This application is also a continuation-in-part of U.S. patent application Ser. No. 15/578,756, filed Dec. 1, 2017, which is a 371 of PCT Application No. PCT/US2016/035503, filed on Jun. 2, 2016, which claimed priority to U.S. Provisional Patent Application Ser. No. 62/169,810, filed on Jun. 2, 2015. These applications are fully incorporated by reference herein.

BACKGROUND

The present disclosure relates to non-invasive methods, systems, and devices for controlling targets, and in particular paralyzed limbs, using a control interface driven by the user's eye movements to control electrical stimulation provided by a neuromuscular electrical stimulation sleeve. In one non-limiting embodiment, the disclosure relates to reanimating a limb, such as a hand, of spinal cord injury patients via non-invasive eye-tracking control of a neuromuscular stimulation system. Various devices and associated components and methods and processes of using the same are further included in this disclosure. It is to be appreciated that these methods, systems, and devices may also be amenable to other like applications.

Many millions of people suffer from some motor impairment. For example, it is estimated that worldwide, 10 million people are left disabled following a stroke each year. People also suffer from brain injury, failed back surgery or spinal cord injury. These injuries can result in motor impairment by damaging the link between the brain and the muscles of the body which are used for movement. For example, neurons in the brain may die, or the nerves between the brain and the muscle are severed. These disrupt the paths by which electrical signals travel from the brain to neuromuscular groups to effectuate coordinated muscle contraction patterns.

Neuromuscular stimulation devices have been used to deliver stimulation to restore movement to parts of the body not under volitional control. For example, subcutaneous implantable neurostimulation cuffs are wrapped around a target nerve and generally include one or more electrodes arranged to stimulate the nerve.

Transcutaneous neurostimulation cuffs behave similarly to implantable cuffs, however there are important differences. Because the electrodes are placed on the surface of the skin, rather than below it, stimulation often can better target skeletal muscle tissue or muscle groups, rather than peripheral nerves located deeper under the skin. Muscular stimulation may be preferable to stimulating major peripheral nerves, e.g. ulnar, median, radial nerves, as stimulating these nerves may cause a patient to feel a tingling sensation and it is more difficult to effect the desired movement. By increasing the number and layout of electrodes in a neuromuscular cuff, current generation neuromuscular stimulation cuffs have been able to selectively stimulate individual muscles or muscle groups and achieve finer movements such as individual finger flexing and extension. Flexible-like transcutaneous cuffs have also been developed which fit around a human appendage such as a forearm to control the wrist or fingers.

Neurostimulation devices do not, by themselves, resolve the problem of motor impairment due to neural damage, because such a device by itself does not respond to volitional control. A system has been previously designed that includes an electrode array that is surgically implanted into the brain. Along with control algorithms, this system has improved motor impairment in a user with a spinal cord injury, conferring on him the ability to grasp, manipulate and release objects and perform functional tasks relevant to daily living. However, the complex surgery to implant the invasive electrode array carries risks and may not be viable for many patients from both a medical and cost perspective. It would be desirable to provide a non-invasive control system that can control electrical stimulation to permit the user to regain volitional control and perform the same type of functional movements as are possible with the invasive system.

BRIEF DESCRIPTION

The present disclosure relates to methods and systems for non-invasive control and movement of a target, such as a limb or prosthetic, by tracking the eye movement of a user to determine the desired movement and delivering one or more electrical signals to obtain the desired movement. These systems include an eye tracking device, a software application that interprets the user's intended movement, and a stimulation system to cause the intended movement to occur.

Disclosed herein are various embodiments of methods of moving a target, comprising: tracking eye movement of a user; based on the eye movement, determining a desired movement of the target; and delivering an electrical signal to the target to obtain the desired movement of the target.

The eye movement can be tracked by a system comprising at least one camera directed towards the eye. Alternatively, the system could be a head-mounted wearable system.

The user may look at a particular icon on a graphical interface to indicate the desired movement. Alternatively, the user might look at the target to indicate the desired movement.

The target of the intended movement can be a body limb or a prosthetic limb, a wheelchair, a cursor on a computer, an exoskeleton, a remote control device, or an external robotic arm. In particular embodiments, the target is a body limb or a prosthetic limb, and the electrical signal is delivered using a neuromuscular electronic stimulation system.

Also disclosed are systems for moving a target, comprising: an eye tracking device; and software that receives eye movement from the eye tracking device as input, determines a desired movement of the target, and outputs an electrical signal to a stimulation system to obtain the desired movement. The stimulation system can be a neuromuscular electrical stimulation sleeve.

These and other non-limiting aspects of the disclosure are more particularly discussed below.

BRIEF DESCRIPTION OF THE DRAWINGS

The following is a brief description of the drawings, which are presented for the purposes of illustrating the exemplary embodiments disclosed herein and not for the purposes of limiting the same.

FIG. 7 is diagram of another exemplary embodiment of a neural sleeve. In this embodiment, conductive pathways extend from two different connectors. The fingers extend in the same direction, and taper towards a center axis.

DETAILED DESCRIPTION

Figure 1A:
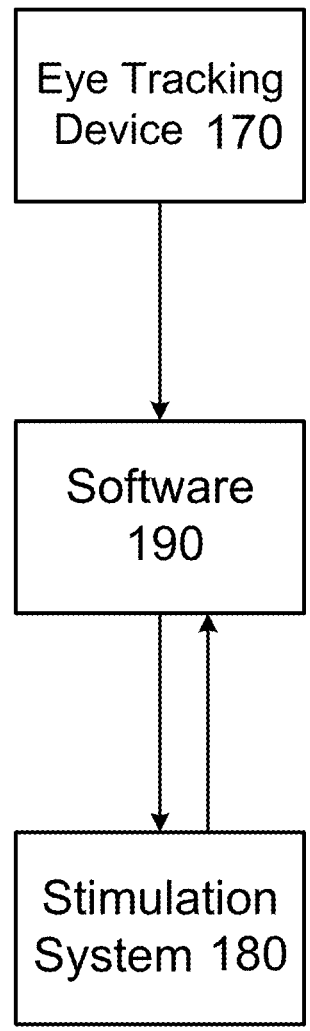
FIG. 1A is a schematic of the overall non-invasive control and movement system.

A more complete understanding of the methods and apparatuses disclosed herein can be obtained by reference to the accompanying drawings. These figures are merely schematic representations based on convenience and the ease of demonstrating the existing art and/or the present development, and are, therefore, not intended to indicate relative size and dimensions of the assemblies or components thereof.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

As used in the specification and in the claims, the terms "comprise(s)," "include(s)," "having," "has," "can," "contain(s)," and variants thereof, as used herein, are intended to be open-ended transitional phrases, terms, or words that require the presence of the named components/ingredients/steps and permit the presence of other components/ingredients/steps. However, such description should be construed as also describing systems or devices or compositions or processes as "consisting of" and "consisting essentially of" the enumerated components/ingredients/steps, which allows the presence of only the named components/ingredients/steps, along with any unavoidable impurities that might result therefrom, and excludes other components/ingredients/steps.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

A value modified by a term or terms, such as "about" and "substantially," may not be limited to the precise value specified. The modifier "about" should also be considered as disclosing the range defined by the absolute values of the two endpoints. For example, the expression "from about 2 to about 4" also discloses the range "from 2 to 4." The term "about" generally refers to plus or minus 10% of the indicated number.

The present disclosure relates to methods for providing an artificial neuromuscular stimulation system with volitional control, e.g. by determine a desired movement of a target by the user, then transmitting the desired movement to the target to perform the desired movement. For example, these methods are useful for patients who may have suffered nerve injury to bypass that disruption and "bridge" that gap to send electrical signals to a body limb, for example an arm or leg. Desirably, it would be as if the disruption did not exist; the patient would simply think of the desired movement of the body limb, and that movement would occur.

In other embodiments, rather than being a body limb, electrical signals may be delivered to a target that is non-human (e.g. an electronic device). This allows for control of the non-human target by use of the electrical signals. Examples of non-human targets that may be controlled in this way include: a prosthetic limb, a wheelchair, a cursor on a computer, an exoskeleton, a remote control device, and an external robotic arm.

In particular, the system includes an eye tracking device that allows the user to control the target using only his eyes. A software application will interpret the user's intent, i.e. the intended movement, and send out electrical signal(s) to produce the desired movement in the target. This type of system is non-invasive, or in other words the user does not have to be surgically operated upon, and no device (like an electrode array) needs to be implanted in the body as in previous iterations of this system.

FIG. 1A is a schematic of the overall non-invasive control and movement system. The overall non-invasive control system 160 is a software/hardware solution that combines an eye tracking device 170, a neuromuscular electrical stimulation system 180, and a custom designed software application 190 to interpret the eye movements into intended movement of a limb and send electrical signals that produce the intended movement. Desirably, this allows a user with a spinal cord injury (SCI) to volitionally execute a variety of grips, as well as wrist and individual finger movements using their own hand.

The software application 190 will receive input from the eye-tracking device 170 that provides information on the intended movement that the user desires. The software application 190 will output control signals to the stimulation system 180, and can also receive feedback from the stimulation system 180 on the movement attained so far, which can be used to adjust subsequent control signals. No invasive surgery is needed, and so for example brain signals from an implanted electrode array are not used in the present disclosure.

The first component of the overall non-invasive control system is a stimulation system that can deliver electrical stimulation. In particular embodiments, the stimulation system is a neuromuscular electrical stimulation system in the form of a sleeve that can be wrapped/attached to the limb of a user, such as the arm or leg. Such systems have been demonstrated to restore functionally significant wrist and hand movements for SCI patients when paired with an intuitive control system. Very broadly, such "neural sleeves" contain a set of electrodes that are used to provide stimulation to the body part when the patient's focus level and intent to move are sufficient. The term "sleeve" is used to refer to a structure that surrounds a body part, for example, an arm, leg, or torso. The neural sleeve can take the form of a shirt, or pants, if desired. The neural sleeve also contains sensors for monitoring movement of the body part (position, orientation, acceleration, etc.), which can be used to track the movement of the body part.

The second component of the overall non-invasive control system is a non-invasive eye-tracking input system. Several different eye-tracking devices are commercially available that may be a practical vehicle for an SCI patient to control a computer. The eye tracking device may include a small camera or multiple cameras attached to the headset positioned on the patient. The camera(s) may also be positioned in any other manner so as to as to be able to view the patients eye's (e.g. the camera(s) may be positioned on a desk, positioned on top of a laptop screen, incorporated into a pair of glasses or so forth). In addition to camera(s) viewing a patient's eyes, camera(s) may also be positioned so that they are pointing outwardly on a pair of glasses that a patient is wearing. This allows a determination to be made of what the patient is looking at, and this information can be used in conjunction with the observations of the patient's eye movements.

The third component of the overall non-invasive control system is a software application that links the user's intent to actual movement. The software application will translate the user's input (i.e. eye movement) into commands for the stimulation that leads to movement of the desired target, e.g. the user's hand. Desirably, the software application will have a clean and intuitive interface that will feel natural to the end user.

Figure 1B:
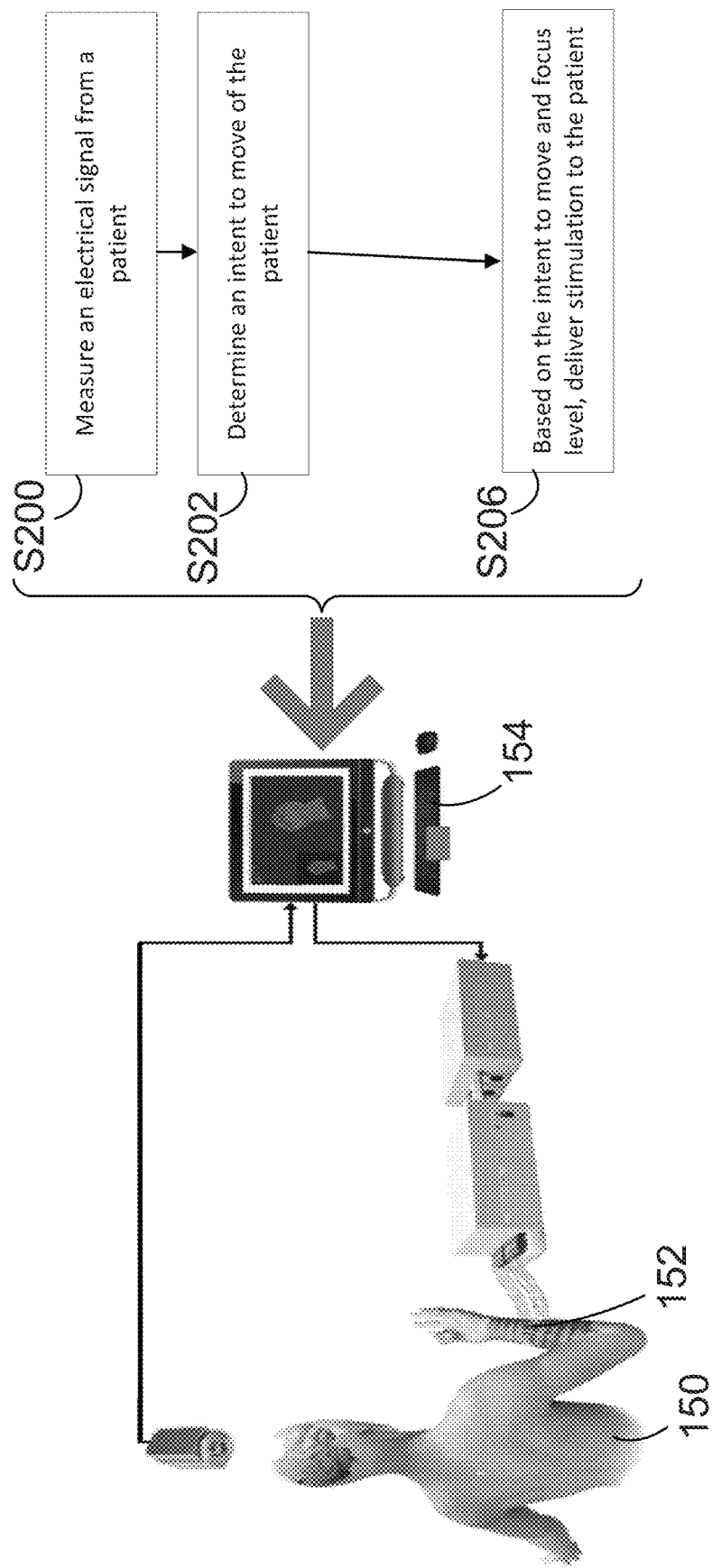
FIG. 1B diagrammatically illustrates one embodiment of the methods of the present disclosure, and a system for practicing the methods.

With reference to FIG. 1B, as a basic overview, the computer or processing unit 154 is connected to receive signals from the eye-tracking input system, and to output control signals to the transcutaneous neurostimulation sleeve 152, and further programmed to determine a volitional intent of the subject based on the received signals and to generate the output control signals to implement that volitional intent. The computer 154 receives the user's eye activity as an input, and determines the desired motion. Based on the analysis done by computer 154, an electrical stimulation pattern is delivered to the user through neural sleeve 154.

In this regard, the present systems monitors the patient's eyes. The patient is asked to move an affected body part (e.g. a limb such as an arm or a leg). The computer monitors the patient's eyes to identify the "signal" of the desired movement. It should be understood that this reference to the desired movement includes a movement being imagined, attempted or executed, depending on the physical capability of the user. It does not require actual movement to occur. The system can provide feedback on how well the patient is doing in generating the signals that would produce the desired movement, through electrical stimulation to the affected body part.

Figure 2:
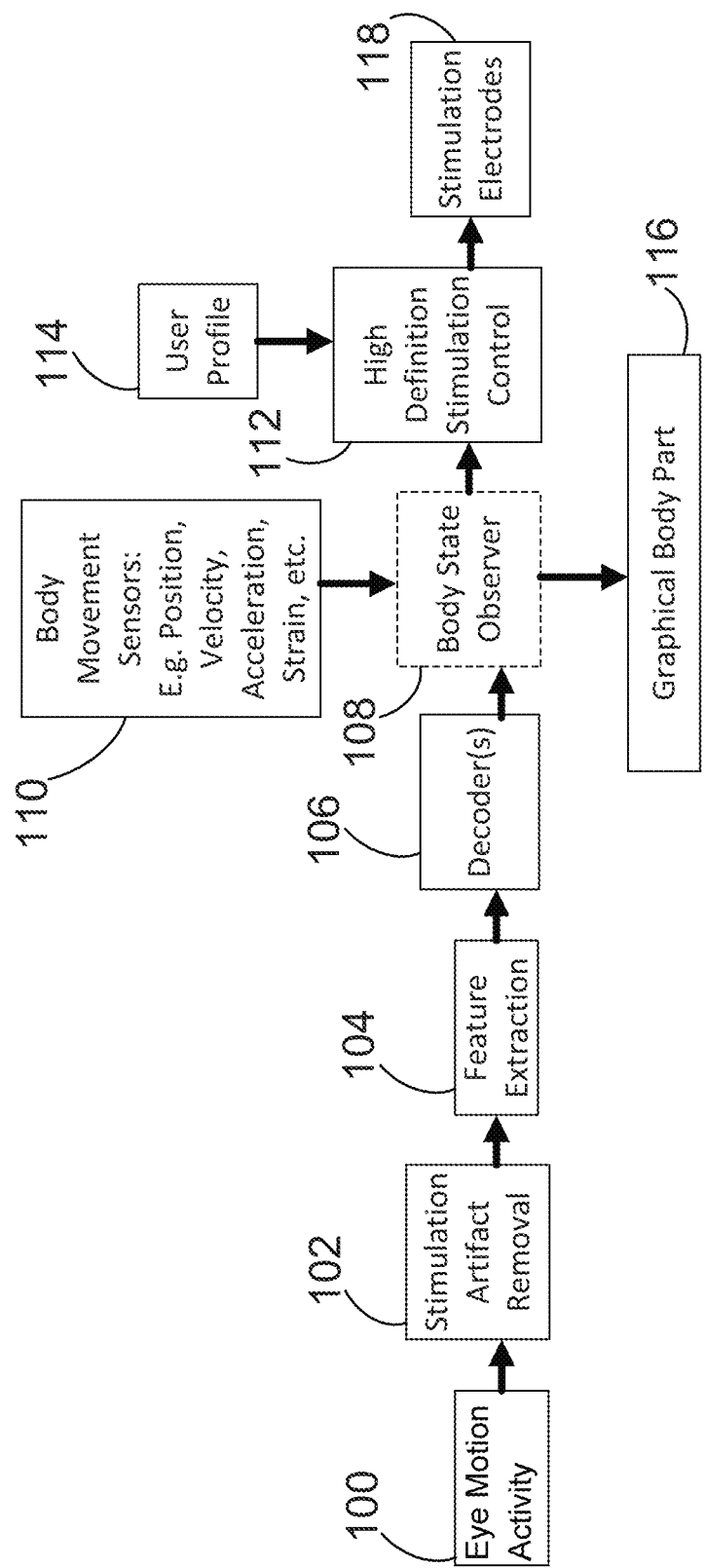
FIG. 2 is a diagram illustrating the methods used in the present disclosure for decoding a neural signal to determine desired movements by a user.

FIG. 2 illustrates a flowchart/algorithm for determining the desired movement from a user's eye-movement activity and translating that into an electrical stimulation pattern that can be transmitted. First, the eye-movement activity of the user 150 is measured in operation 100 to obtain an input signal. Noise artifacts are then removed from the input signal in operation 102. To determine the desired movement, one or more features are extracted from the measured input signal in operation 104. Subsequently, the extracted feature(s) are sent to decoders in operation 106. The decoders determine the imagined movement. That output is then sent to a body state observer 108, which is a model of the various parts of the user's body. Inputs from body movement sensors 110 may also be taken into account in the body state observer 108, which is used to predict future movements that need to be made to obtain the desired movement. In operation 112, high definition stimulation control is used to calculate the stimulation pattern that is needed to obtain the desired movement. A user activation profile 114 containing information on the user's reaction to various stimulation patterns can be used here to customize the resulting stimulation pattern/signal that is determined. That stimulation pattern is then sent to stimulation electrodes 118, which stimulate the appropriate part of the body part (e.g. muscle groups, etc.). Alternatively, the system calculates the effect such stimulation would have, and displays this in the form of a graphical body part 116, to provide feedback to the user. This algorithm repeats at a high rate, permitting continuous real-time updating of the stimulation signal to the target. Thus, it should be understood that the methods described herein may be performed either continuously or intermittently.

Returning to FIG. 1B, the methods implemented by the software are described on the right-hand side. First, as shown in step S200, the patient's eye-movement activity is measured. As previously described, this measurement can be performed by analysis of the data provided by the eye-tracking input system. The eye-movement signals can be sampled at appropriate rates, providing a robust stream of data (though not all of this data needs to be used). These eye-movement signals are sent wirelessly or, alternatively, through a wired connection, to a signal processing device for processing.

After measurement, the eye-movement signals indicating the patient's intent are analyzed. The video data captured by the camera(s) may be processed to obtain information. Such information may include, for example, what the patient is looking at, how long the patient has been looking at a particular location, etc. Based on these features, the patient's intent to move is determined in operation S202.

Based on the intent to move, electrical stimulation is delivered to the patient in operation S206. This electrical stimulation can be delivered to at least the body part that the patient is trying to move. This provides some feedback to the patient.

If desired, the system can vary the amplitude of the delivered stimulation (electrical current level) as a function (proportionally, linearly, or non-linearly) of the eye-movement signal/features being monitored.

Returning now to FIG. 2, it may be helpful to discuss each action that occurs in interpreting the eye-movement signals received and generating electrical stimulation for the body part that is to be moved.

As previously mentioned, the eye-movement activity of the user 150 is measured in operation 100 to obtain an input signal. Next, the input signal is processed 102 to obtain a "clean" signal. For example, extraneous or undesired signals (such as blinking) need to be removed. The signal may be processed in analog or digital form, and generally results in one or more electrical signals.

Figure 3:
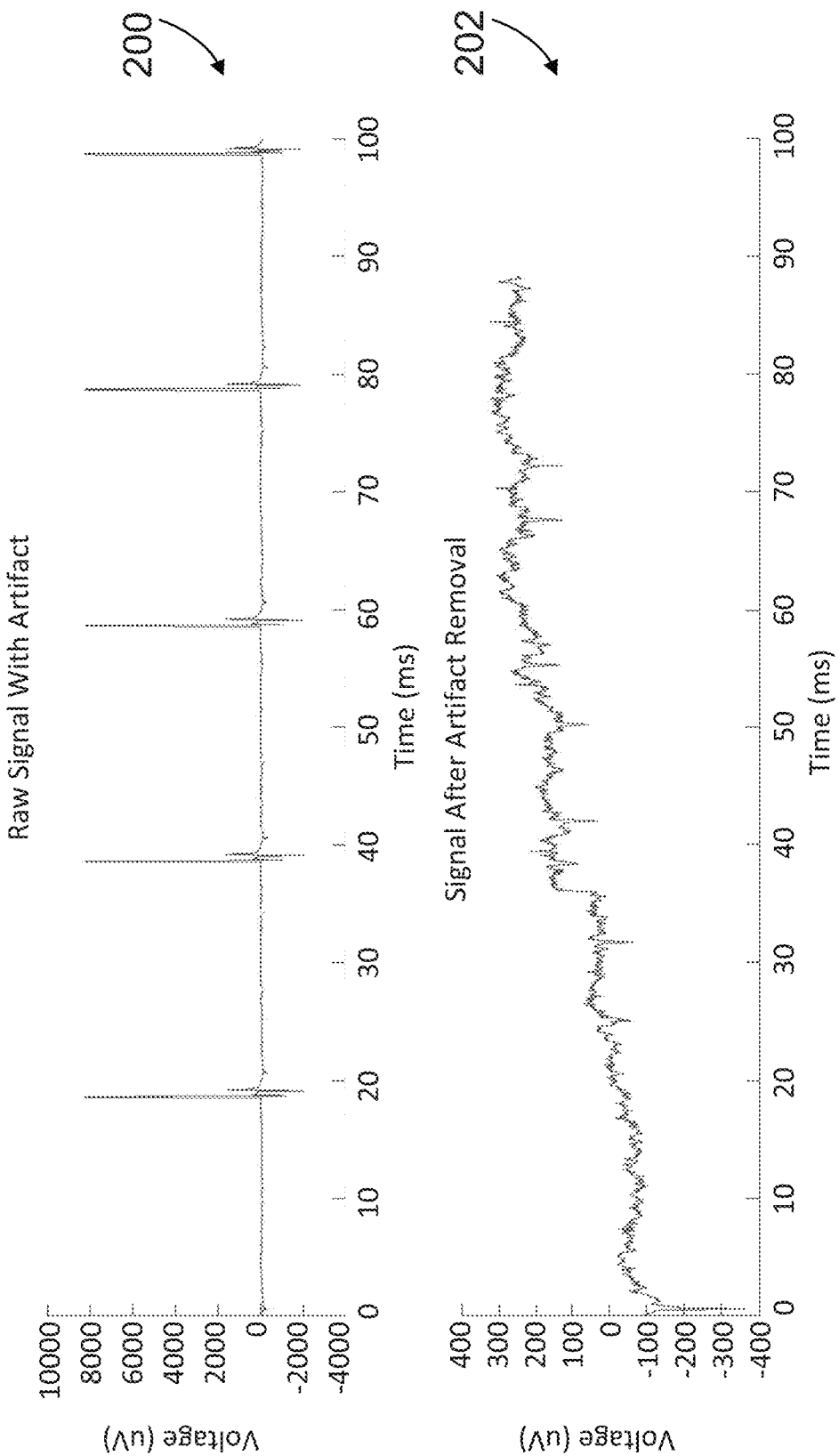
FIG. 3 illustrates a neural signal before and after artifact removal. In the "before" graph at top, the y-axis is voltage in microvolts, with the scale ranging from −4000 to +10,000 μV at intervals of 2000 μV. The x-axis is time, with the scale ranging from 0 milliseconds (msec) to 100 milliseconds at intervals of 10 msec. In the "after" graph at bottom, the y-axis is voltage in microvolts, with the scale ranging from −400 to +400 μV at intervals of 100 μV. The x-axis is time, with the scale ranging from 0 milliseconds (msec) to 100 milliseconds at intervals of 10 msec. It can be seen that the "before" time has been processed such that the "end" time is of a shorter duration (about 10% shorter), which is due to removal of signal artifacts.

Part of the processing 102 involves artifact removal. Artifact removal is used to "clean up" the data and results in improved processing. Artifacts in the data may have been caused by, for example, electrical stimulation in the body limb (e.g. forearm) whose movement is desired. FIG. 3 shows a signal before artifact removal 200, and shows the "same" signal after artifact removal 202. Identification of an artifact may be accomplished by, for example, by detecting a threshold crossing in the signal data. Here, for example, the artifacts are the extremely high peaks up to 8000 µV at periodic rates of ~20 msec. The threshold can be fixed or dynamically calculated, and for example can be modified based on factors already known to the processor such as when electrical stimulation is delivered through the neurostimulation sleeve. A set time window of data may then be removed around the detected artifact. The data is then realigned (e.g. voltage-wise) and then stitched back together (e.g. time-wise). For example, as shown here, the time window is 2.5 milliseconds, based on the system's recovery period for an amplifier. The five peaks are thus removed, and the remaining signal is shown on the bottom. As seen here, once the artifacts are removed, the signal is of much smaller magnitude but contains useful information.

Of course, when data is being measured on multiple channels (e.g. from several different cameras), the artifact should be removed on each channel. One common method of artifact removal is to determine the average from all or most of the channels, and then subtract the average from each channel. Alternatively, the stimulation signal can be shaped in such a way that artifacts on certain frequencies may be prevented or reduced. In other embodiments, the artifacts can be planned somewhat. For example, the electrical stimulation delivered through the neurostimulation sleeve 152 could have a known shape, such as a square pulse. These will aid in removing artifacts from the neural signal.

Next, in operation 104 of FIG. 2, features are extracted from the input signal. "Feature" is the term given to various pieces of data that can contain useful information for determining the desired movement. Examples of such features include: the item/location being looked at, the length of time the item/location has been looked at, a change in the item/location being looked at, signal amplitude, power level, etc. Again, the extracted features provide useful information about the desired movement, or the actual movement that is occurring.

In some applications, a Fast Fourier Transform (FFT) may be used to extract features. Advantageously, an FFT may be used for obtaining power information. Additionally, a non-linear or linear transform may be use to map the features to N-dimensional space (e.g. by use of a radial basis function). This may be useful when a desired movement can manifest itself in the form of multiple different electrical signals, so that the system can recognize any of those different signals.

Next, the extracted features are sent to one or more decoders 106 that associate the features with a particular action, movement, or so forth. It is contemplated that decoders can be implemented in at least two different ways. First, as illustrated in FIG. 4A, the extracted features may be sent as input to individual decoders 300. Each decoder has previously been "trained" to associate certain features with a particular movement. Examples of such decoded motions include: individual finger flex or extension; wrist flex or extension; radial deviation; forearm supination or pronation; and hand open or close. Each decoder then outputs a binary yes/no output as to whether its particular movement has been identified. Advantageously, use of the decoders allows for a determination of related, simultaneous movements. For example, the decoders may determine that the user desiring to close a hand with either the arm moving or not moving. Also, the training dataset used to build the decoder may only maintain a certain amount of history, so that the decoder may adapt to changes in the eye-movement signals over time.

Figure 4B:
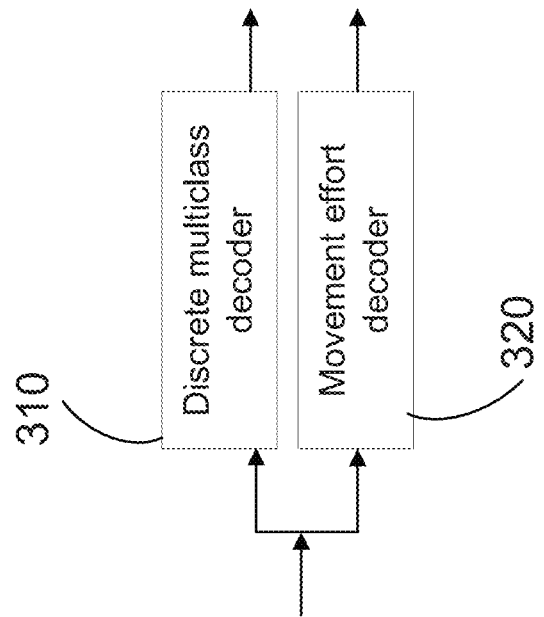
FIG. 4B shows a discrete multiclass decoder and a movement effort decoder. The multiclass decoder can be considered an amalgamation of the single-motion decoders illustrated in FIG. 4A. The movement effort decoder outputs a measure of the focus level being applied to attain the desired movement.
Figure 4A:
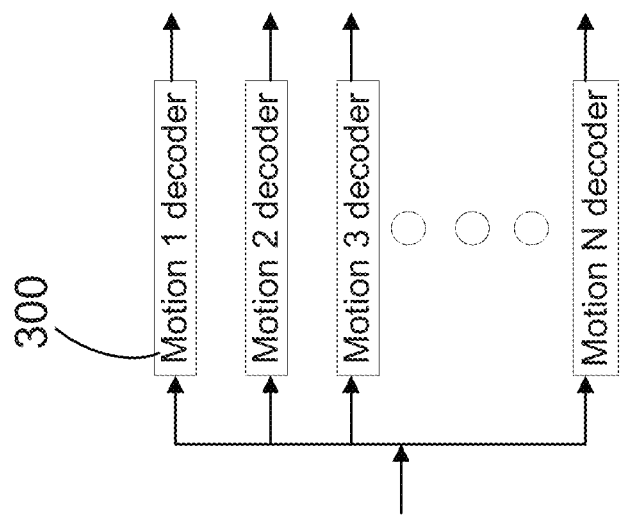
FIG. 4A is a diagram indicating single-motion decoders, which provide simple binary output (yes/no) to identify a desired movement.

Alternatively, as illustrated in FIG. 4B, the decoders can be organized in the form of a discrete multiclass decoder 310 that is used in parallel with a movement effort decoder 320. The discrete multiclass decoder determines the motion(s) that is being imagined. For purposes of this disclosure, the multiclass decoder can be considered as a software module that receives the features as input, and can output any one of multiple desired movements. The movement effort decoder determines the level of movement effort of the identified movement(s). Any decoded signal may be linearly or non-linearly mapped to determine a signal delivered to the target. In general, the system can determine both the user's movement intention before the physical movement begins, and also during movement as well. Again, it should be noted that the eye-movement signals from the user are for movements that may be imagined or attempted, as well as actually performed.

Next, the output of the decoders is sent to a "body state observer" 108. The body state observer is a physics-based dynamic model of the body (e.g. including body parts such as arm, hand, leg, foot, etc.) implemented as software. The body state observer takes the desired forces, torques or so forth as inputs and continuously updates and outputs the velocity and position estimates of the actual body part(s). The body state observer can also accept data from body movement sensors 110 as input. Such sensors may provide information on the position, velocity, acceleration, contraction, etc. of a body part. For example, sensors could provide information on the position of the elbow relative to the shoulder and the wrist, and how these body parts are moving relative to each other. In addition, the body state observer has a "memory" or a history of the feedback previously provided to the user.

The use of a body state observer is considered to have at least two advantages. First, the outputs of the body state observer can be used to continuously or dynamically change the stimulation patterns being outputted to the neurostimulation sleeve, to account for changed circumstances. For example, if the stimulation electrodes are transcutaneous, they can move with respect to their target muscles as the joints move (e.g. pronation/supination). The stimulation pattern given through the stimulation electrodes can thus be modified according to the relative shift between electrodes and muscles. In other words, the stimulation pattern may be dynamically changed (or held constant) based on a determined body state. This dynamic change in the stimulation pattern may be referred to as electrode movement compensation (EMC). In one example of EMC, a stimulation pattern may be changed based on whether a user's palm is up or down. Second, for transcutaneous electrodes and even implanted electrodes, the force or torque at a given stimulation current is often a function of joint position, velocity, or so forth. As the observer predicts joint position and velocity, the stimulation current can be adjusted accordingly to maintain a force or torque desired by a user.

Examples of body states considered by the body state observer include palm up or palm down; arm moving or not moving; a flexing, extension or contraction of a wrist or other body part; and positions or movements of joints.

As another example, the body state observer can use the decoder outputs to estimate angular force at the joints corresponding to the desired motion using a model of the hand and forearm with 18 degrees of freedom. The model estimates the force caused by the contraction of the muscle, the force opposing the muscle contraction due to the anatomy of the hand and forearm, a damping force, and the force of gravity. The output of the model is an estimate of the position of the hand and forearm in real-time, taking into account the history of the stimulation provided to the forearm in order to estimate a current position of the hand and forearm.

The electrical stimulation pattern that is to be sent to the stimulation system by the software application (third component) is determined by an encoding algorithm that generates the appropriate spatiotemporal patterns to evoke appropriate muscle contractions. The present disclosure permits high definition stimulation. In high definition stimulation, the simulation pattern to the electrodes is "continuously" updated. For example, the stimulation pattern to the electrodes is updated once every 0.1 seconds (e.g. 10 Hz). However, shorter and longer update times are also contemplated; in fact, speeds up to 50 Hz are contemplated. As discussed above, the simulation pattern is provided based on the desired movement, and can be adjusted based on body states determined by the body state observer. To create a smoother motion, a nonlinear or linear mapping may be applied to the output of the decoder(s). The user's particular user activation profile 114 can also be used to modify or determine the electrical signal that is sent to the target. In this regard, different patients need a different stimulation pattern to obtain the same movement of the target. Advantageously, this allows for delivery of a more effective stimulation pattern based on the individual characteristics of a user. The stimulation pattern is then sent to the stimulation system, which can for example use electrodes 118 to stimulate the muscles needed to achieve the desired movement.

In high definition stimulation, multiple signal patterns may be interleaved (e.g. by multiplexing) if more than one motion is desired (e.g. a compound motion). For example, the stimulation pattern needed to lift the arm may be directed to different muscles than those for rotating the wrist. Interleaving permits multiple stimulation patterns to be combined into a single stimulation signal sent to the stimulation system (e.g. neuromuscular sleeve), so that multiple movements can occur at the same time. Again, this permits the body limb to move more naturally. In addition, advantageously, interleaving prevents electric field patterns created by one stimulation pattern from interfering with electric fields created by another stimulation pattern. This increases the number of complex motions that the system is capable of. However, there is a practical limit to the number of stimulation patterns that may be interleaved due to the fact that when the pulse rate for a single simulation pattern becomes too low (e.g. less than 10 pulses per second), muscle twitches will start to become noticeable and movement smoothness becomes undesirable. Still, interleaving is very effective, and allows for multiple movements to be performed simultaneously (e.g. in a compound movement). This could not be achieved with only a single simulation pattern.

In addition, motions may be sequenced. One example of this in a natural system is a central pattern generator, which produces rhythmic patterned outputs without sensory feedback. The software/systems of the present disclosure can mimic central pattern generators by producing a repeatable sequence of events, for example to return a targeted body part to an initial state. Another example of sequenced motions is a functional series of motions. Examples of functional series of motions include: teeth brushing, scratching, stirring a drink, flexing a thumb, cylindrical grasping, pinching, etc. These motions allow for manipulation of real-world objects of various sizes.

As a result of the stimulation, the target/body part moves as imagined by the user, which can serve as feedback to the user. The electrical stimulation can be provided in the form of current-controlled, monophasic pulses of adjustable pulse rate, pulse width, and pulse amplitude which can be independently adjusted for each channel. This cycle repeats continuously. The stimulation signal/pattern sent to the electrodes can be changed continuously through each cycle if needed, or can be maintained, in order to complete the imagined movement. The software can monitor either or both the eye movement and the motion of the target as detected by the sensors. The stimulation signal sent to the target may be actively changed over time due to changes in motion/location, for example due to the shift in the electrode position relative to their targeted muscle groups as a body limb moves. Desirably, the decoder is also robust to context changes (such as arm position and speed).

It is contemplated that the eye-tracking device and the software application can work together to determine the desired movement. For example, various icons could be displayed on a graphical user interface (GUI) that indicate certain motions, e.g. flex the wrist, extend the wrist, lift the arm perpendicularly, etc. The user could stare at the icon corresponding to the desired motion, with the time spent staring at the icon being used as an indicator of the degree of motion (e.g. how much to flex the wrist), or a scale indicating the degree of motion could be located next to the icon. Alternatively, the user could stare at the body part whose movement is desired, and the GUI could then present movement options.

Figure 5:
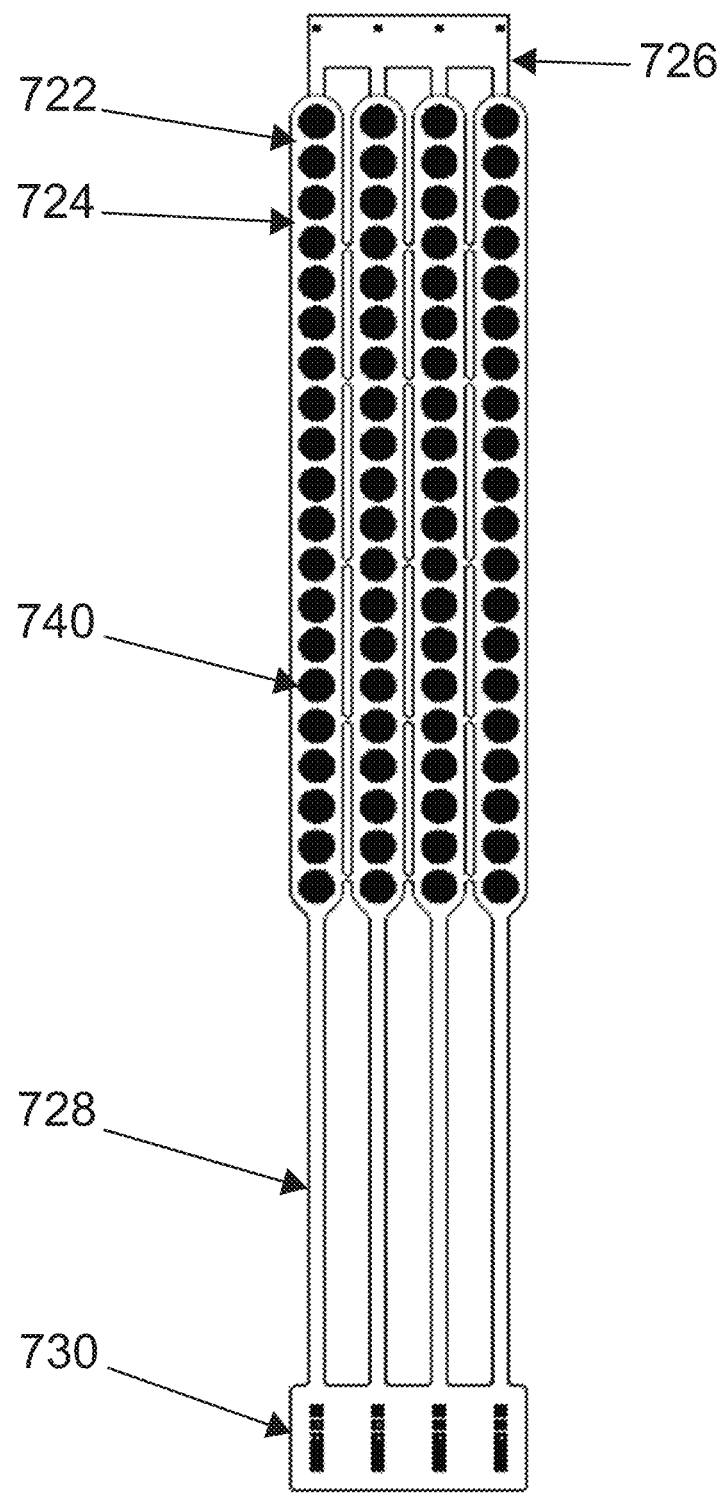
FIG. 5 is a plan view of one embodiment of a neural sleeve that can be used for practicing the methods of the present disclosure.

FIG. 5 is an illustration of one potential neural sleeve that can be used as a stimulation system in the methods of the present disclosure. The sleeve 700 as illustrated has an insulating substrate 722 that is shaped into four flexible conductive pathways 710, each pathway being formed from a finger 724 and a header 728. The flexible conductive pathways 710 extend in the same direction from the connector 730, which acts as a connector for one end of the pathways. In other words, the ends of the pathways distal from the connector are all located in the same direction relative to the connector, or put another way the connector 730 is at one end of the device. It is noted that the pathways 710 are shown here as extending at a 90-degree angle relative to the connector 730. The pathways can be attached to each other, for example by five webbings 725 which run between adjacent fingers 728.

The electrodes 740 are located or housed on the fingers 724, and are formed as a layer upon the substrate 722. The electrodes 740 run along the four fingers 724 and are electrically connected to the connector 730. The electrodes 740 are approximately 12 mm in diameter and spaced 15 mm apart. A conductive medium, e.g. hydrogel discs, can be laid upon the electrodes to facilitate contact with the user's skin.

The connector 730 is used for interfacing with the software application/computer 180 of FIG. 1A. If desired, an optional fork 726 can be located at the end of the pathways opposite the connector 730. The fork connects all of the fingers, and can be provided for structural support for design and mounting. Headers 728 extend between the connector 730 and the fingers 724. These headers are thinner than the fingers, and connect the fingers 724 to the connector 730. The headers are also part of the overall flexible conductive pathway, though they are not always required. Though not illustrated, webbings can also be provided between adjacent headers as well if desired. Again, the fork 726 is optional, though the connector 730 is required.

Figure 6:
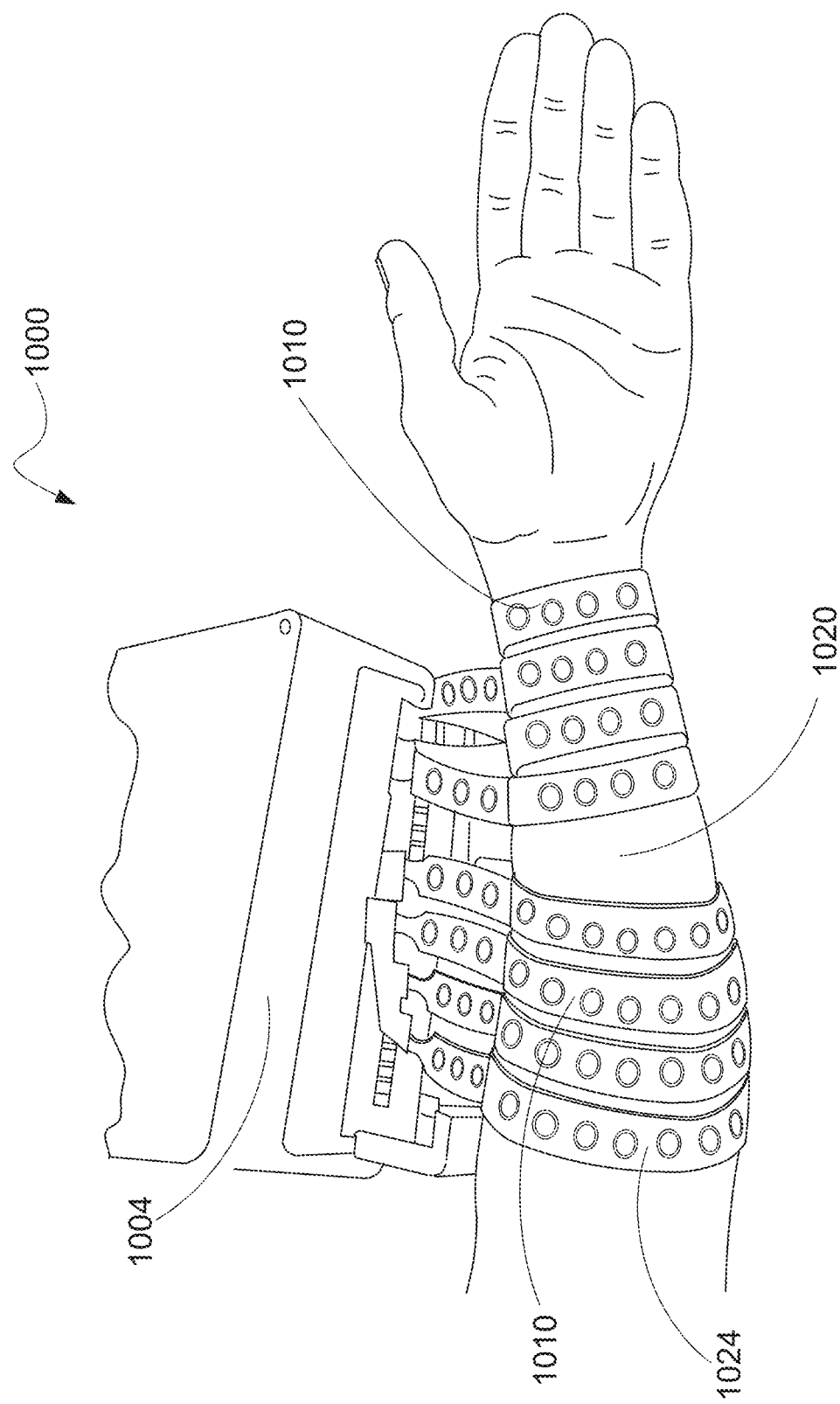
FIG. 6 is an exemplary photograph showing two neural sleeve devices according to the embodiment of FIG. 5 which are wrapped around a patient's arm region in preparation for neuromuscular stimulation.

FIG. 6 shows two neuromuscular cuff devices 1010 of FIG. 5 being wrapped circumferentially around a patient's arm region 1020 in preparation for neuromuscular stimulation. The two cuff devices 1010 together provide 160 separate electrodes for stimulating finger or wrist movements. The fingers 1024 permit the neuromuscular cuff to fit around the arm region 1020 at points of varying circumference. Hydrogel discs 1016 (not shown) keep both cuffs 1010 adhered to the arm.

In another exemplary embodiment, the flexible conductive pathways on a neural sleeve 2110 do not need to be straight for their entire length. Referring now to FIG. 7, flexible conductive pathways 2124 extend from first connector 2130, which has a rectangular shape in this illustration. The flexible conductive pathways 2124 in this embodiment "change" directions as they extend from connector 2130. For example, an upper flexible conductive pathway 2124a first extends upwards from the connector 2130, then changes direction so that its electrodes 2140 are to the right of the connector 2130. A center flexible conductive pathway 2124b extends from the right-hand side of the connector 2130 off to the right of the connector. A lower flexible conductive pathway 2124c first extends downwards from the connector 2130, then changes direction so that its electrodes 2140 are also to the right of the connector 2130. Notably, none of the electrodes 2140 are present to the left of the connector 2130.

This embodiment of a neural sleeve 2110 also contains more than one connector. As illustrated here, the neural sleeve 2110 has a first connector 2130 and a second connector 2131. Flexible conductive pathways extend in the same direction (here, to the right) of both connectors. Webbings 2135 connect flexible conductive pathways extending from each connector 2130, 2131. There may be any number of webbings 2135, and the webbings 2135 may connect the flexible conductive pathways at any portion of their length. Here, the webbings 2135 are present along a a non-electrode-containing portion 2150 of the flexible conductive pathways (i.e. the header portion). Though not depicted, it is specifically contemplated that the flexible conductive pathways of one connector 2130 may be of a different length from the flexible conductive pathways of the other connector 2131.

The electrodes 2140 may be evenly spaced apart along the length of the flexible conductive pathways 2124, or their spacing may vary, for example becoming shorter or longer, as the distance from the connector 2130 increases. For example, muscle segments get smaller closer to the wrist, so the electrodes need to be closer together as well. However, the electrodes do not need to be present along the entire length of the flexible conductive pathways. As seen here, the flexible conductive pathways 2124 may include a non-electrode-containing portion 2150 extending from the connector. The flexible conductive pathway may also include a non-scalloped electrode-containing portion 2160, and a scalloped electrode-containing portion 2170 at the distal end of the flexible conductive pathway (i.e. distal from the connector). It should be noted that none of the flexible conductive pathways overlap with each other.

The electrode-containing portions 2160, 2170 of the flexible conductive pathways have a different shape from each other. One reason for this difference in shape is because, as seen here, the distal ends of the flexible conductive pathways 2124 extend inwardly towards a center axis 2105 of the neural sleeve 2110. Put another way, the flexible conductive pathways 2124 taper inwards towards the center axis 2105. The scalloped portions 2170 of adjacent flexible conductive pathways permit them to fit into a smaller area while still providing a suitable number of electrodes (note the electrodes do not change in size). However, the flexible conductive pathways 2124 all still extend in the same direction away from the connector 2130, i.e. to the right in this figure. Put another way, the flexible conductive pathways comprise a first portion which is transverse to the center axis 2105, and a second portion which is parallel to the center axis. These portions are particularly seen in the flexible conductive pathway 2124a, which first extends upwards (i.e. transversely to the center axis), then extends parallel to the center axis.

This particular embodiment is intended to be used on a patient's arm with the two connectors 2130, 2131 located near the shoulder, and the scalloped portions 2170 near the wrist and hand.

It is also contemplated that the neural sleeve may be wireless (e.g. communicate with computer 154 wirelessly). The neural sleeve may also be battery-based. This could be accomplished, for example, by strapping a battery or control pack in an iPhone-like carrier to a patient arm, patient leg, belt, or so forth.

The overall non-invasive control system should be able to execute various grips that are important for tasks of daily living, for example picking up objects, pouring the contents of one container into another, swiping a credit card, and playing a video game. These would be significant improvements in motor-impaired individuals. Additional improvements could include controlling two separate sleeves, one on each arm, using the eye-tracking device and software.

It will further be appreciated that the disclosed techniques may be embodied as a non-transitory storage medium storing instructions readable and executable by a computer, (microprocessor or microcontroller of an) embedded system, or various combinations thereof. The non-transitory storage medium may, for example, comprise a hard disk drive, RAID or the like of a computer; an electronic, magnetic, optical, or other memory of an embedded system, or so forth.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. A method of moving a target, comprising:
tracking eye movement of a user;
based on the eye movement, determining a desired movement of the target and a desired degree of motion of the target; and
delivering an electrical signal to the target to obtain the desired movement of the target;
wherein the user looks at a particular icon of a plurality of icons representing movement options presented on a graphical interface to indicate the desired movement; and
wherein the user stares at the particular icon to indicate the desired degree of motion of the target as a time spent staring at the icon or the user looks at a scale presented on the graphical interface to indicate the desired degree of motion of the target.

2. The method of claim 1, wherein the eye movement is tracked by a system comprising at least one camera directed towards the eye.

3. The method of claim 1, wherein the system is a head-mounted wearable system.

4. A method of moving a target, comprising:
tracking eye movement of a user;
based on the eye movement, determining a desired movement of the target; and
delivering an electrical signal to the target to obtain the desired movement of the target;
wherein the user looks at the target whose movement is desired and in response a graphical interface presents a plurality of icons on the graphical interface representing movement options and the user looks at a particular icon of the plurality of icons representing the movement options to indicate the desired movement of the target.

5. The method of claim 1, wherein the target is a body limb or a prosthetic limb, a wheelchair, a cursor on a computer, an exoskeleton, a remote control device, or an external robotic arm.

6. The method of claim 5, wherein the target is a body limb and the electrical signal is delivered using a neuromuscular electronic stimulation system.

7. A system for moving a target, comprising:
an eye tracking device;
a neuromuscular electrical stimulation sleeve; and
a computer that receives eye movement comprising at least one eye movement signal from the eye tracking device as input, and is programmed to perform artifact removal on the at least one eye movement signal to remove artifacts including detecting an artifact in the at least one eye movement signal caused by operation of the neuromuscular electrical stimulation sleeve and removing a time window of data around the detected artifact, and determine a desired movement of the body limb based on the at least one eye movement signal after artifact removal, and output an electrical signal to the neuromuscular electrical stimulation sleeve to obtain the desired movement.

8. The method of claim 6, wherein the tracking of eye movement of the user includes measuring at least one eye movement signal, and the determining of the desired movement of the target is based on the at least one eye movement signal and comprises performing artifact removal on the at least one eye movement signal to remove artifacts including detecting an artifact in the at least one eye movement signal caused by the delivery of the electrical signal using the neuromuscular electronic stimulation system and removing a time window of data around the detected artifact.

9. The method of claim 1, wherein the user stares at the particular icon to indicate the desired degree of motion of the target as a time spent staring at the icon.

10. The method of claim 1, wherein the user looks at a scale presented on the graphical interface to indicate the desired degree of motion of the target.

11. The system of claim 7, wherein the detecting of the artifact in the at least one eye movement signal caused by operation of the neuromuscular electrical stimulation sleeve includes detecting a threshold crossing in the at least one eye movement signal.

12. The method of claim 1, wherein the determining of the desired movement of the target and the desired degree of motion of the target is based only on the eye movement.

13. The method of claim 4, wherein the determining of the desired movement of the target is based only on the eye movement.

14. The method of claim 7, wherein the computer determines the desired movement of the body limb based only on the at least one eye movement signal.

* * * * *